United States Patent
Barnett et al.

[11] Patent Number: 5,980,535
[45] Date of Patent: Nov. 9, 1999

[54] APPARATUS FOR ANATOMICAL TRACKING

[75] Inventors: Gene H. Barnett, Gates Mills, Ohio; Christopher H. Wood, Bellevue, Wash.; Patrick A. Dayton, Monroe Falls, Ohio

[73] Assignee: Picker International, Inc., Highland Heights, Ohio

[21] Appl. No.: 08/935,796

[22] Filed: Sep. 23, 1997

Related U.S. Application Data

[60] Provisional application No. 60/027,402, Sep. 30, 1996.

[51] Int. Cl.$^6$ .................................................. A61B 17/00
[52] U.S. Cl. ........................................ 606/130; 128/653.1
[58] Field of Search .................... 606/130; 128/653.1, 128/653.4

[56] References Cited

U.S. PATENT DOCUMENTS

| | | |
|---|---|---|
| 4,991,579 | 2/1991 | Allen . |
| 5,269,034 | 12/1993 | Day et al. . |
| 5,383,454 | 1/1995 | Bucholz . |
| 5,517,857 | 5/1996 | Chader et al. . |
| 5,517,990 | 5/1996 | Kalfas et al. . |
| 5,730,130 | 3/1998 | Fitzpatrick et al. ..................... 606/130 |
| 5,752,962 | 5/1998 | D'Urso .................................. 606/130 |

FOREIGN PATENT DOCUMENTS

| | | |
|---|---|---|
| 297 07 917 | 7/1997 | Germany . |
| WO 94/24933 | 11/1994 | WIPO . |
| WO 96/10368 | 4/1996 | WIPO . |

OTHER PUBLICATIONS

Starrett Product Catalog, Printed Sep. 1996, pp. 466–473.

*Primary Examiner*—Michael Buiz
*Assistant Examiner*—William Lewis
*Attorney, Agent, or Firm*—Timothy B. Gurlin; John J. Fry; Eugene E. Clair

[57] ABSTRACT

A position signaling is usable in connection with an image guided surgery system. A plurality of infrared emitters are mounted on a reference object. The reference object is in turn attached to the rocker arm of a head clamp. The head clamp includes a frame and a first head engaging pin secured to one side of the frame. The rocker arm includes two head engaging pins and is movable in relation to the frame. The image guided surgery system uses the signals provided by the infrared emitters to determine and account for movement of the patient's head.

32 Claims, 8 Drawing Sheets

APPARATUS FOR ANATOMICAL TRACKING

This application is a continuation-in-part of provisional U.S. application Ser. No. 60/027,402 filed Sep. 30, 1996.

BACKGROUND

The present invention relates to the medical diagnostic and surgical arts. It finds particular application in conjunction with neurosurgery and will be described with particular respect thereto. It will be appreciated, however, that the invention finds application in conjunction with biopsies, endoscopic procedures, orthopedic surgeries, other medical procedures, industrial quality control procedures, and the like in which a tool or device must be accurately positioned in relation to an object.

Image guided surgery systems are particularly well adapted to intra-cranial and spinal surgery. These systems use diagnostic images of the patient to assist the physician with presurgical planning and to provide information relating to the position and orientation of the anatomy and instrumentation during a surgical procedure. Image guided surgery systems are well-suited for use in connection with magnetic resonance ("MR") and computerized tomography ("CT") images, as well as with other imaging modalities.

In cranial applications, a patient reference frame may defined using three or more points fixed in relation to the patient's head. According to one method, at least three markers visible to the imaging device are affixed to the skin prior to imaging. According to another method, anatomical reference points are used. According to a third method, fiducial markers may be affixed to the skull, for example as disclosed in U.S. Pat. No. 4,991,579, *Method and Apparatus for Providing Related Images of the Anatomy over time of a Portion of the Anatomy Using Fiducial Implants,* to Allen, issued Feb. 12, 1991. Similar techniques may be used to define a patient reference frame with respect to other portions of the anatomy.

An image of the patient having an image reference frame is then obtained. Based on the location of the three or more markers within the image data, the image and patient reference frames can be correlated. Hence, the position of a feature of interest within the image can be determined with respect to the patient reference frame. After image acquisition is complete, the patient can be moved as desired. The patient is subsequently placed in an operating room environment, for example on an operating table.

A localizer, which defines an operating room reference frame, is used to determine the position of a surgical tool. The tool includes a plurality of emitters having a known relationship to the tip of the tool. Based on the signals detected by the cameras, the position of the tool with respect to the operating room reference frame may be determined.

The patient and operating room reference frames are correlated or "zeroed" by touching the surgical tool to the at least three markers. The position of the tool with respect to the cameras, and hence the position of the markers, is then determined. Inasmuch as the relationship between the patient, operating room, and image frames of reference is known, the position of the tool with respect to the image reference frame can then be determined. Relevant images, with the position of the surgical tool indicated thereon, are then displayed on a monitor. The surgeon is thus provided with a real time indication of the position of the surgical tool with respect to the previously obtained image.

In spinal applications, the patient reference frame is preferably defined in relation to anatomical reference points such as the transverse and spinous processes. The patient and operating room reference frames are correlated by touching the surgical tool to the reference points.

The position of the patient ordinarily remains fixed with respect to the localizer. Should the position of the patient change, however, the patient and operating room frames of reference must be re-correlated by touching the tip of the probe to the at least three markers.

As an alternative, the position of the patient may be continuously monitored through the use of one or more emitters having a known position with respect to the patient. By determining the position of the emitters with respect to the localizer, the patient and operating room reference frames may be automatically re-correlated to account for movement of the patient.

U.S. Pat. No. 5,383,454 (the "'454 Patent") to Bucholz, entitled *System for Indicating the Position of a Surgical Probe Within a Head on an Image of the Head,* discloses an apparatus usable with a BRW head ring. A reference ring is attached to the head using sharp pins. Prior to imaging, a cylindrical reference frame is attached to the reference ring. Image data is obtained with the head encircled by the frame. By determining the position of the reference frame in the image data, the relationship between the data and the reference ring may be determined. Prior to surgery, the reference frame is removed from the reference ring and replaced with a base ring containing a plurality of emitters. The position of the emitters is then monitored by localizer, and the operating room and patient reference frames are automatically re-correlated to account for movement of the patient.

A drawback to the apparatus disclosed in the '454 Patent is that the reference ring and frame are bulky, obtrusive, and uncomfortable. As a result, the reference ring and frame are generally worn for only a short period of time. Further, the reference ring complicates the surgeon's access to the patient's anatomy. Yet another drawback is that an additional clamping device is needed to immobilize the patient's head during surgery. Again, however, the structure of the reference ring requires that the head clamp be designed and positioned to avoid mechanical interference with the reference ring.

The '454 Patent also notes that the reference ring and frame may be eliminated by using surgical screws affixed to the patient's skull to identify reference points on the patient's body and suggests that the emitters may each be separately mounted to a screw or other fixed structure positioned at one of the reference points.

A drawback to this approach is that it complicates the mechanical structure of the screws or pins attached to the reference points. Not only must the screws be visible in the scanned image and facilitate accurate correlation of the various reference frames, the screws must also accommodate attachment of the emitter structure. At the same time, it is desirable that the screws be as unobtrusive as possible. Further, the screw or screws must be positioned so that the emitter structure does not interfere with the head clamp and so that the emitters communicate reliably with the localizer.

U.S. Pat. No. 5,269,304 (the "'034 Patent") to Day, et al., entitled *Surgical Head Clamp* discloses a head clamp which is marketed under the Mayfield® trademark by Ohio Medical Instrument Company, Inc. of Cincinnati, Ohio. With particular reference to FIG. 2 and column 2 line 36 to column 3 line 26 of the '034 Patent, expressly incorporated by reference herein, the head clamp includes an adjustable, generally c-shaped frame (reference numeral 12 in the '034

Patent). The clamp also includes three head engaging pins, two of which are mounted on a rocker arm (reference numeral 28 in the '034 Patent), which is in turn adjustably mounted to the c-shaped frame 12. The clamp is in turn attached to a structure such as the operating table.

Reference emitters have been mounted on a structure clamped to the operating table. When mounted to the operating table, however, the emitters are useful for providing information as to movement of the table but fail to provide information as to movement of the patient with respect to the table. Reference emitters have also been mounted to the c-shaped frame 12 of the clamp described in the '034 Patent and thus provide tracking of the clamp position together with an indication of the position of the patient's head. However, the clamp includes various adjustments which facilitate positioning of the clamp and the patient, as well as various mechanical connections between adjacent parts. Each of these adjustments and connections has the potential to allow relative motion between the emitters and the patient such that movement of the patient may not be accurately reflected in the position of the c-shaped frame 12, or vice versa.

SUMMARY

The present invention addresses the above-referenced shortcomings, and others.

According to a first aspect of the present invention, a position signaling apparatus is adapted for use with a surgical head clamp which includes a frame and a first head engaging pin secured to one side of the frame. The position signaling apparatus includes a pin holding means mountable to an opposite side of the frame. The pin holding means adapted to support second and third head engaging pins. The position signaling apparatus also includes a position signaling device supported by the pin holding means. The signaling device is adapted for operative communication with an image guided surgery system.

According to a more limited aspect of the present invention, the position of the signaling device in relation to the pin holding means is selectively adjustable.

According to another more limited aspect of the present invention, the position signaling apparatus includes means for attaching the signaling device to the pin holding means. According to a still more limited aspect, the means for attaching includes a clamp attached to the pin holding means.

According to yet another more limited aspect of the present invention, the apparatus also includes an adjustable support structure which attaches the position signaling device to the pin holding means. The adjustable support structure includes first and second members and a joint which connects the first and second members and allows relative pivotal motion of the first and second members. According to a still more limited aspect, the joint selectively allows relative motion of the joint and the first member along the longitudinal axis of the first member. According to another still more limited aspect, the joint selectively allows relative rotational motion of the first member and the joint about the first longitudinal axis. According to yet another more limited aspect, the apparatus includes a third member and a second joint which interconnects the second and third members. The joint selectively allows relative pivotal motion between the second and third members.

The members may comprise rigid, cylindrical rods, and the joint may comprise a clamp.

According to yet another more limited aspect of the present invention, the pin holding means includes a mounting boss and the position signaling device is supported by the mounting boss. According to still another aspect of the present invention, the position signaling device includes a plurality of infrared emitters.

According to another aspect of the present invention, a method of determining the position of a surgical head clamp is provided. The head clamp includes a frame, a first head engaging pint secured to one side of the frame, and a pin holding means mounted to an opposite side of the frame. The pin holding means supports second and third head engaging pins mounted to the pin holding means. The method includes the steps of attaching a position signaling device adapted for operative communication with an image guided surgery system to the pin holding means and using the image guided surgery system to determine the position of the position signaling device.

According to a more limited aspect of the present invention, the position signaling device is connected to a support structure. The method further comprises the step of clamping the support structure to the pin holding means. According to a still more limited aspect, the pin holding a mounting boss and the support structure is clamped to the mounting boss.

According to another more limited aspect of the present invention, the step of attaching the position signaling device to the pin holding means includes the step of inserting the end of a support member in a through hole on the pin holding means.

According to another more limited aspect of the present invention, the pin holding means includes a mounting boss. The step of attaching the position signaling device to the pin holding means includes the steps of connecting a first rod to the mounting boss, connecting a second rod to the first rod, connecting the second rod to a third rod, and connecting the third rod to the position signaling device, and adjusting the position signaling device in relation to the pin holding means.

According to another aspect of the present invention, an apparatus is adapted to determine the position of an object disposed in a clamp which includes a frame, a first object engaging pin disposed on one side of the frame, and pin holding means movably mounted to an opposite side of the frame. The pin holding means is adapted to support second and third object engaging means mounted thereon. The apparatus includes a position signaling device disposed in fixed relation to the pin holding means for movement therewith and means for determining the position of the signaling device.

According to a more limited aspect of the present invention, the position of the signaling device in relation to the pin holding means is selectively adjustable. According to another more limited aspect of the present invention, the means for determining comprises an infrared localizer.

According to yet another more limited aspect of the invention, the apparatus includes a mounting structure which attaches the position signaling device to the pin holding means. The mounting structure includes a plurality of connected cylindrical rods. The connections between the rods selectively allow the rods to be rotated about their longitudinal axes, the connections further selectively allowing relative pivotal motion of adjacent connected rods. According to a still more limited aspect of the invention, the connections selectively allow the rods to be moved along their longitudinal axes.

According to another aspect of the present invention, a position signaling apparatus for use with an image guided surgery system is provided. The apparatus includes a position signaling device adapted for operative communication with the image guided surgery system and an adjustable support structure. The adjustable support structure includes a first member connected to the position signaling device, a second member, and a joint disposed between and connecting the first member and second members. The joint selectively allows relative pivotal motion of the first and second members.

According to a more limited aspect of the present invention, the second member may be readily disconnected from the first member.

Still other advantages will be appreciated by those skilled in the art upon reading and understanding the appended description.

DRAWINGS

DESCRIPTION

Figure 1:
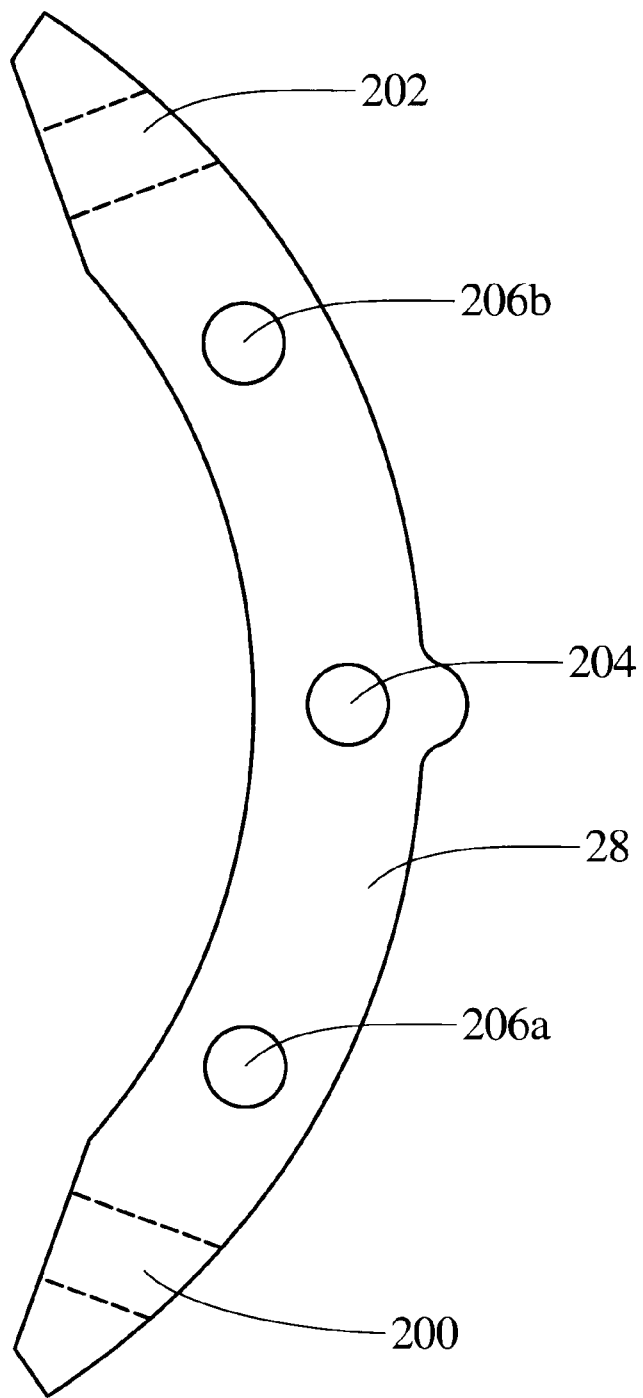
FIG. 1 depicts a rocker arm according to the present invention.

The present invention is preferably operated in conjunction with an image guided surgery system such as disclosed in commonly assigned U.S. Pat. No. 5,517,990 (the '990 Patent"), *Stereotaxy Wand and Tool Guide,* to Kalfas, et al. issued May 21, 1996 and expressly incorporated by reference herein. In a preferred application, an infrared localizer is used rather than the ultrasonic localizer of the '990 Patent. The infrared localizer includes detectors such as two spaced apart infrared cameras to define an operating room reference frame. The cameras are mounted in a generally stationary location, for example on the operating table, on the ceiling or wall, or on a stand.

A surgical tool, guide, or other device for use with the infrared cameras includes at least three infrared emitters having a known relationship to the tip or other feature of the tool. Additional emitters may also be used to permit continued tracking of the device in the event that the line of sight between one or more of the emitters becomes interrupted and to provide increased accuracy. Depending on the characteristics of the localizer, fewer emitters may also be used. Based on the signals detected by the cameras, the position of the surgical tool or device with respect to the operating room reference frame can be determined. Thus, the localizer system can be used to determine the position of at least one surgical tool.

The present invention will be described with reference to FIGS. 1 through 9 herein and FIG. 2 of the '034 Patent. Features common to FIGS. 1 through 9 and FIG. 2 of the '034 Patent will utilize common reference numerals.

Figure 2:
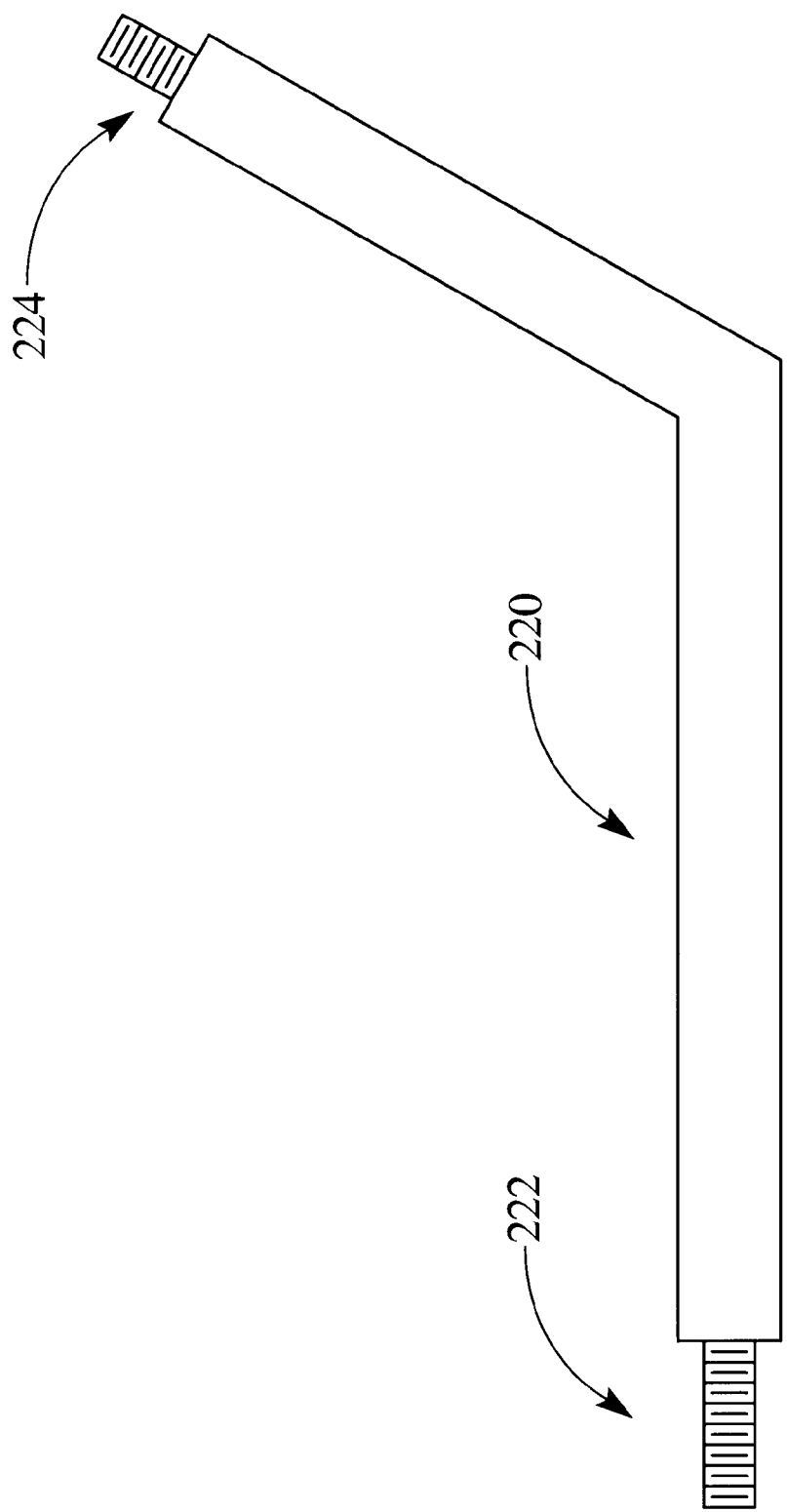
FIG. 2 depicts a mounting arm according to the present invention.

With reference to FIG. 2 of the '034 Patent and FIG. 1 herein, a head clamp 12 includes a generally c-shaped rocker arm 28. The rocker arm 28 includes apertures 200 and 202 which accept head engaging pins 30 and 32, respectively. A third aperture 204 facilitates pivotal attachment of the rocker arm 28 to a support 34 and ultimately to the frame 14. The rocker arm 28 also includes through holes 206a and 206b.

Figure 3:
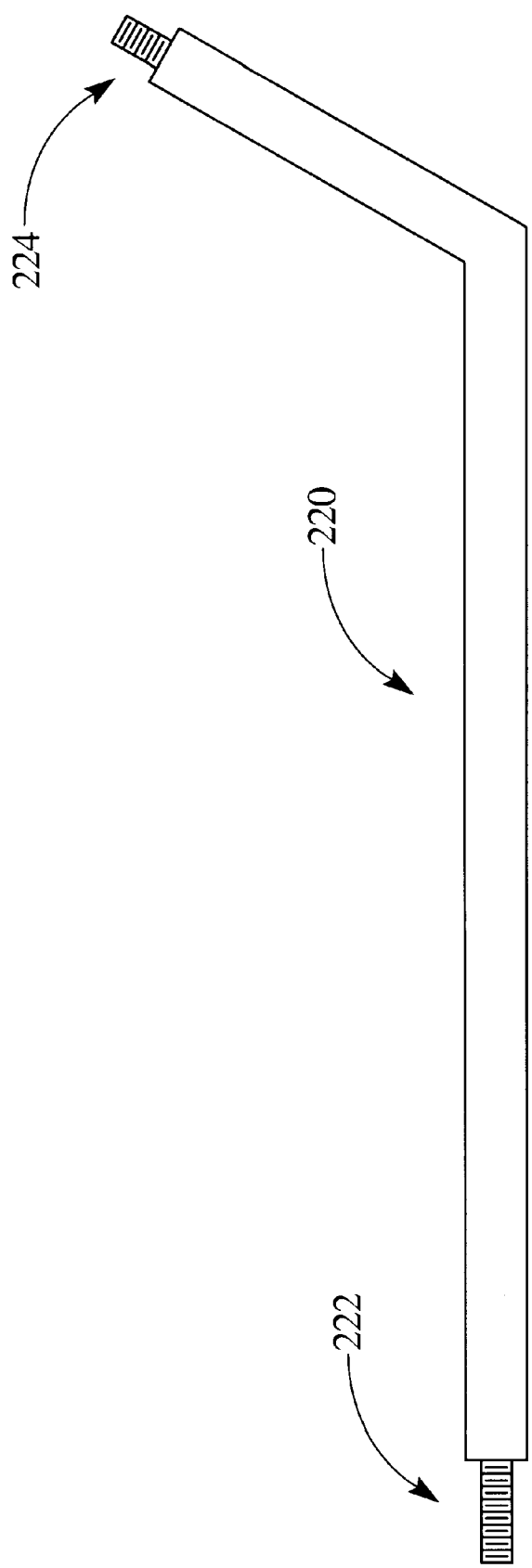
FIG. 3 depicts a second mounting arm according to the present invention.

Mounting arms for use with the rocker arm 28 are shown in FIGS. 2 and 3 herein. The mounting arms 220 contain first 222 and second 224 threaded ends. The first end 222 is inserted through one of the through holes 206a and 206b and secured in position with a nut. Of course, the mounting arm 220 may be affixed to the rocker arm 10 by any suitable means, including by welding, screws, clamps, or the like. The configuration of mounting arm 220 (e.g. its lengths and angles) is selected to permit access to the patient while providing a suitable line of sight for the localizing device. It will also be appreciated that the mounting arms may take other forms, for example taking the form of an adjustable Greenberg clamp. The desired orientation of the mounting arm 220 with respect to the rocker arm 28 is ordinarily determined prior to tightening the nut which holds it in place.

Figure 4:
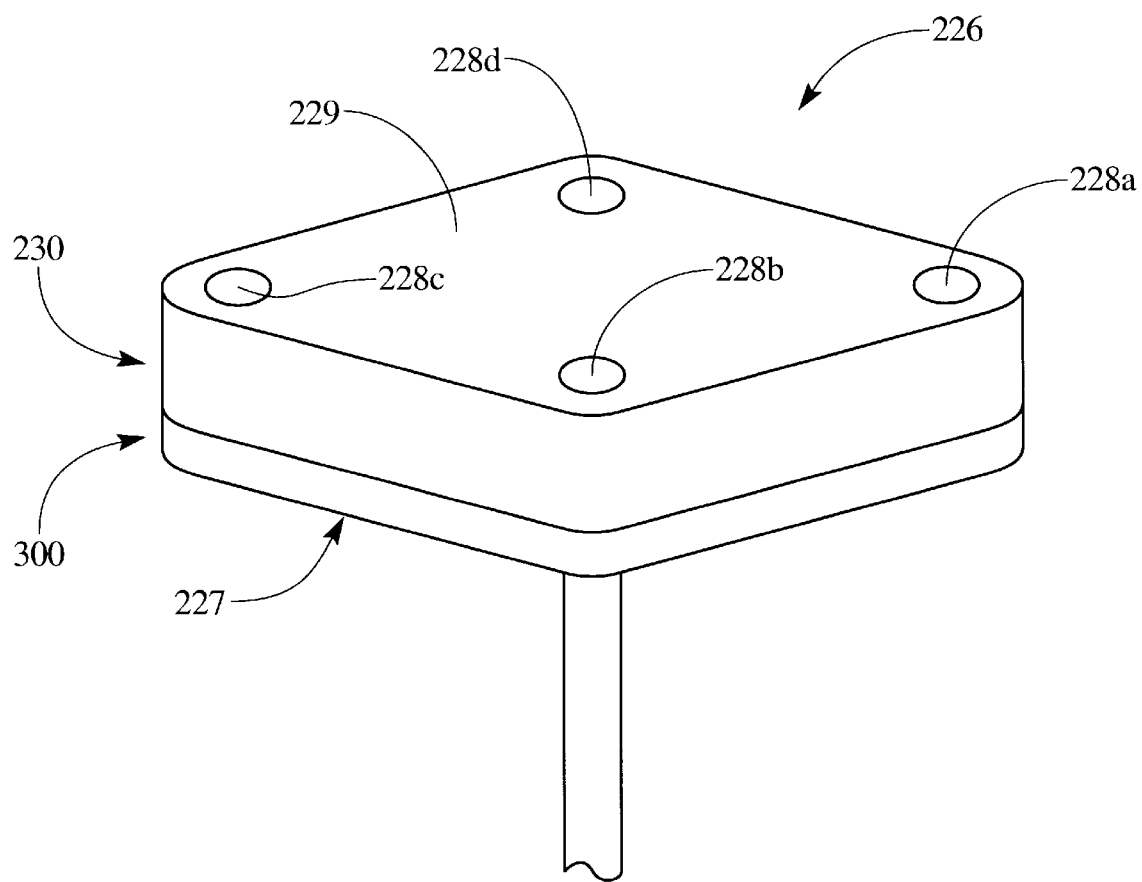
FIG. 4 depicts a reference object according to the present invention.
Figures 5A, 5B:
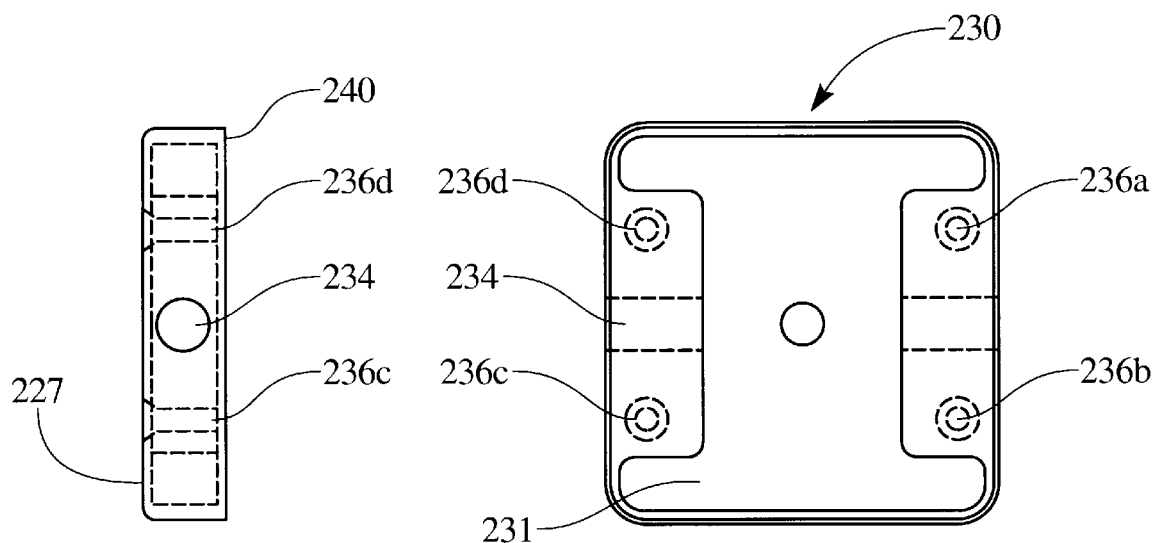
FIG. 5a is a top view of the body of a reference object according to the present invention.
FIG. 5b is a side view of the body of a reference object according to the present invention.
Figure 7:
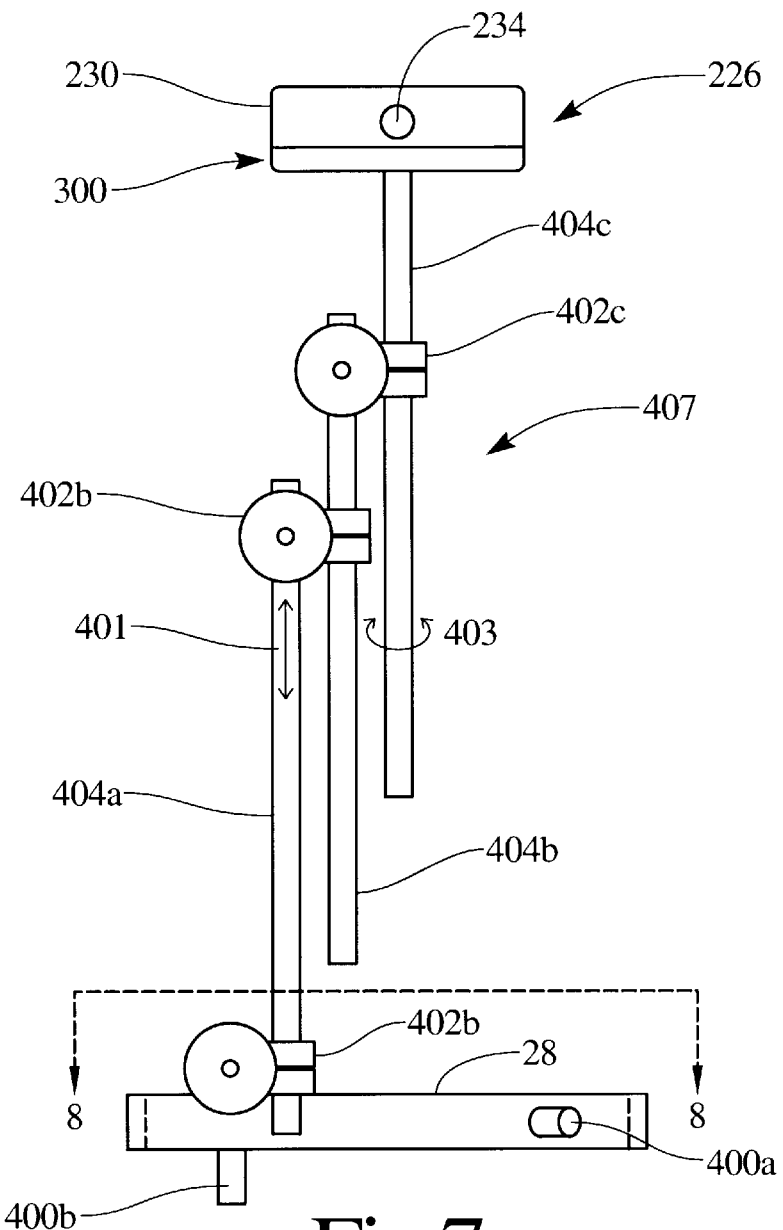
FIG. 7 depicts a trackable rocker arm according to the present invention.

With reference to FIGS. 4 and 7, a position signaling device such as reference object 226 is adapted for use an image guided surgery system. The top surface 229 of the reference object 226 includes four infrared emitters 228a–228d. Depending on the characteristics of the localizer, fewer emitters may also be used. While the reference object 226 is described as including infrared emitters for use with an infrared localizer, it will be appreciated that alternate devices, such as infrared detectors, sonic receivers or transmitters, electromagnetic devices, reflective elements, or the like may be used depending on the requirements of the particular localizer system. Similarly, the positions of the emitters and detectors may be interchanged. With reference to FIGS. 4 and 5a, the bottom surface 227 of the reference object 226 includes a threaded aperture 232 which accepts the second end 224 of the mounting arm 220. Thus, the reference object 226 may be mounted in a desired position in relation to the rocker arm 28.

Because the location of the emitters 228a–228d with respect to the reference object 226 is known, the position and orientation of the reference object 226 may be accurately tracked using the localizer. The reference object 226 is characterized prior to use, i.e. the precise positional relationship between the emitters 228a–228d and the reference object 226 is determined and stored in memory. In a preferred embodiment, the information is stored in a programmable memory mounted inside the reference object 226. Alternatively, the memory could be located in a connecting cable, digitizer, or computer system.

With references to FIGS. 5a and 5b, the reference object 226 includes a body 230. In the embodiment illustrated in FIG. 5, the bottom surface of the body 230 contains the threaded aperture 232 and forms the bottom surface 227 of the reference object 226. The body 230 also defines a cavity 231 which houses requisite wiring and the programmable memory. Wiring ingress and egress is through a wiring aperture 234.

Figure 6A:
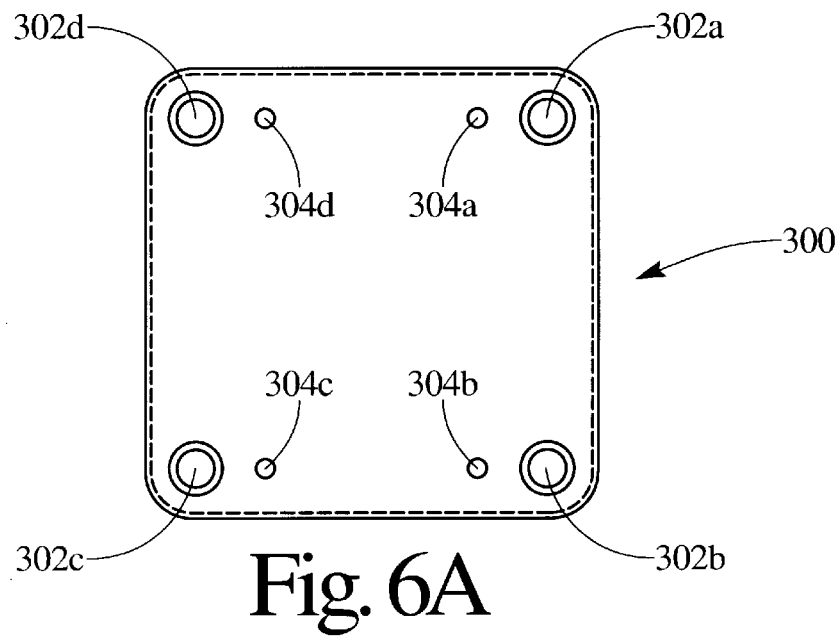
FIG. 6a is a top view of a cover for a reference object according to the present invention.
Figure 6B:
FIG. 6b is a side view of a cover for a reference object according to the present invention.

With continuing reference to FIGS. 5a and 5b and further reference to FIGS. 6a and 6b, a cover 300 includes emitter apertures 302a–302d into which the emitters 228a–228d may be mounted. The cover 300 mates with the body 230 and is fastened thereto using screws which extend through screw holes 236a–236d and engage corresponding blind holes 304a–304d. In the embodiment of FIGS. 5 and 6, the cover 300, when installed, forms the upper surface 229 of the reference object 226.

The body 230 and cover 300 may also take other configurations. In a particularly advantageous alternate configuration which is illustrated in FIGS. 4 and 7, the threaded aperture 232 forms part of the cover 300, while the emitter apertures are located on the opposite surface of the body 230 so that the emitters 228a–228d are mounted to the body 230. Thus, the body 230 forms the upper surface 229 of the reference object 226 while the cover 300 forms the lower surface 227. Installation of the emitters 228a–228d and routing of wiring is thereby simplified, while the overall configuration of the reference object 226 remains unchanged.

Figure 10:
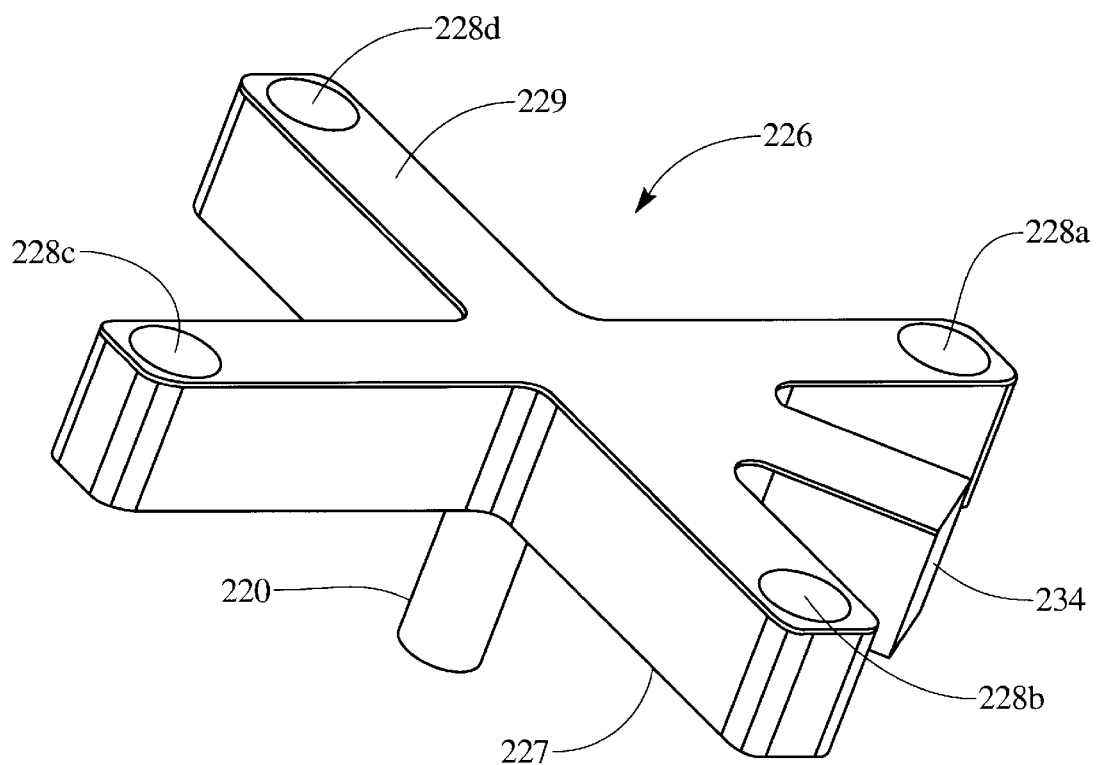
FIG. 10 depicts a reference object according to the present invention.

While the reference object has been described as having a generally block-like shape, the emitters may be affixed to an structure having alternate configurations such that the emitters are maintained in a desired spacing and configuration. With reference to FIG. 10, the reference object 226 has a generally x-shaped configuration. Emitters 228a–228d are disposed on the upper surface 229 of the reference object 226. A mounting boss 220 extends from the bottom 227 of the reference object 226 to simplify attachment. Wiring ingress and egress is through a wiring aperture 234.

Figure 8:
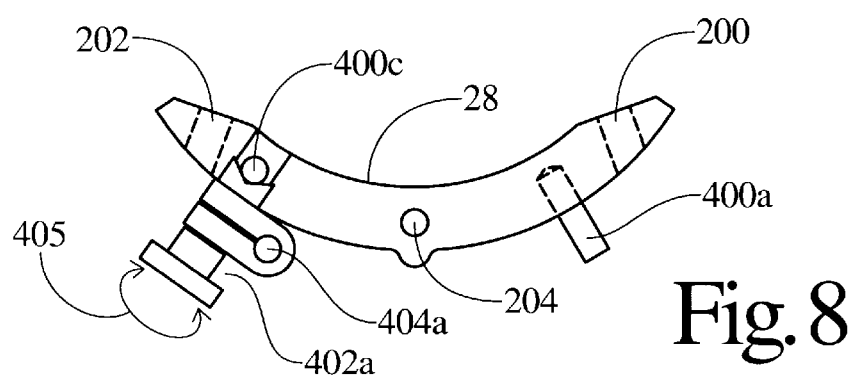
FIG. 8 is a sectional view along line 8—8 of FIG. 7.

An alternate embodiment of an apparatus according to the present invention is shown in FIGS. 7 and 8. With reference to FIG. 8, the rocker arm 28 includes reference device attachment structures such as cylindrical mounting bosses 400a, 400b, 400c. Of course, the number and location of bosses may be varied as desired. Through holes 206 and mounting bosses 400 may both be included on the rocker arm 28 to provide additional flexibility. An adjustable mounting structure 407 facilitates adjustment of the position and orientation of the reference object 226 in relation to the rocker arm 28.

A first adjustable mounting clamp 402a engages one of the mounting bosses, for example mounting boss 400c. The mounting clamp 402a also engages a first rigid cylindrical extension rod 404a. A second mounting clamp 402 also engages the first cylindrical extension rod 404a. The second mounting clamp 402b in turn engages a second rigid cylindrical extension rod 404b. A third mounting clamp 402c also engages the second rod 404b. The third mounting clamp 402c in turn engages a third rigid cylindrical mounting rod 404c. Threads on rod 404c engage the threaded aperture 232 on the bottom of the reference object 226.

The mounting clamps 402 function as joints which allow the position of the rods 404 to be adjusted. The clamps 402 preferably allow a variety of degrees of motion. First, the clamps 402 allow the rods 404 inserted therein to be moved longitudinally in the direction of arrow 401. The clamps 402 also allow relative rotation of the rods 404 and clamps 402 about the longitudinal axis of the rods 404 as indicated by arrow 403. The clamps 402 also permit relative pivotal motion of the rods 404 inserted therein the direction of arrows 405. Thus, the position and orientation of the reference object 226 may be readily adjusted.

While the mounting structure is illustrated with three rods 404 and associated clamps 402, the rods 202 are readily insertable in and removable from the clamps 402 such that greater and lesser numbers of rods may be used, further enhancing the adjustability of the reference object 226 in relation to the rocker arm 28. Similarly, rods of different lengths or configurations (i.e. having bends or curves) may be substituted. In this regard, it should be noted that the adjustable mounting structure 407 is usable in connection with devices other than the rocker arm 28 and the reference object 226. Thus, for example, the mounting structure 407 may be used to allow relative positioning between a reference object and a surgical microscope, or to allow positioning of a surgical tool in relation to a stationary structure.

Figure 9:
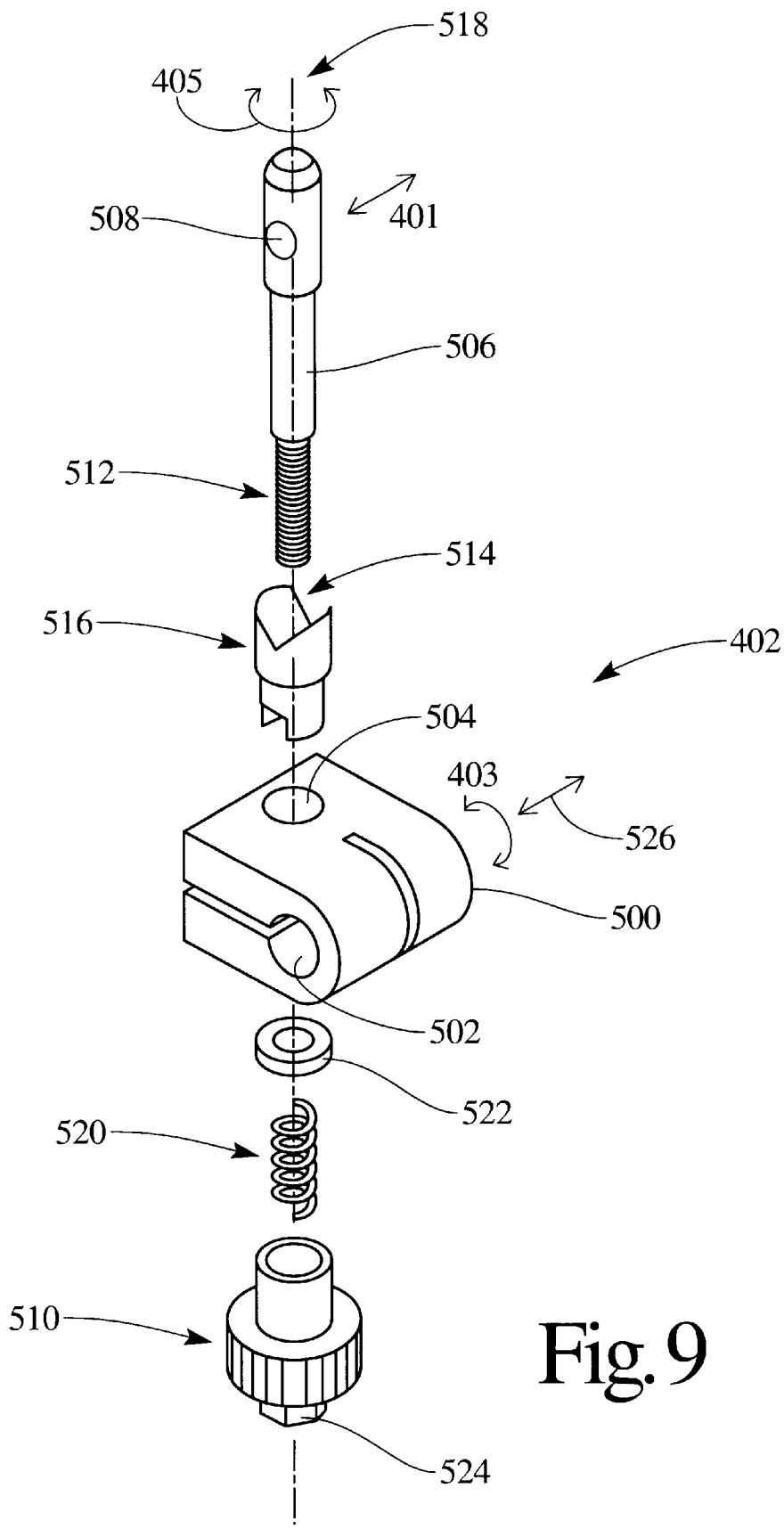
FIG. 9 is an exploded view of an adjustable clamp according to the present invention.

With reference to FIG. 9, a clamp 402 has a clamp body 500 having orthogonal, non-intersecting apertures 502 and 504. Aperture 502 accepts a rod 202 for insertion therethrough, while aperture 504 accepts a rod-engaging member 506. The rod-engaging member 506 also contains an aperture 508 which accepts a rod 202 for insertion therethrough. A thumb screw 510 engages threads 512 on the rod-engaging member 506. The thumbscrew also includes a hexagonal extension 524. A v-shaped groove on a rod-holding member 514 frictionally engages a rod 202 inserted in the aperture 508. Both the rod-engaging member 506 and the rod-holding member 516 are rotatable within the aperture 504 about axis 518 as indicated by the arrows. A spring 520 placed in compression urges the thumb screw 510 and hence the rod-engaging member 506 downward so that the aperture 508 is urged toward the clamp body 500. The end of the rod-engaging member 506 is sized to prevent the member 506 from being urged all the way through the aperture 504. A washer 522 is disposed between the spring 520 and the clamp body 500.

The clamps 402 thus permit the positions of rods 202 inserted in the apertures 508 and 502 to be selectively adjusted. When the thumbscrew 510 is loosened, a rod 202 inserted in the aperture 502 is movable along its longitudinal axis through the aperture 502 as indicated by arrows 206. The rod 202 is also rotatable within the aperture 502 in the direction indicated by arrows 403. Similarly, a rod 202 inserted in the aperture 508 is movable along its longitudinal axis through the aperture 502 in the direction of arrows 401. The rod 202 is also rotatable within the aperture 508 in the direction indicated by arrows 405. The rods may also be pivotally adjusted relative to each other as indicated by arrow 405. With the thumb screw 524 loosened, rods inserted in the apertures 508 and 502 may be readily removed from and inserted in the apertures. Tightening the thumb screw 504 holds the rods 202 more securely in place. The clamp 502 may also be tightened more firmly using a tool in conjunction with hexagonal extension 524.

In operation, the reference object 226 is attached to the rocker arm 28 and its position adjusted to provide reliable communication between the emitters 228a–228d and the localizer and so that the reference object and the associated supporting structure does not interfere with the activities of the surgeon. The patient and operating room reference frames are initially correlated by touching the tip of a the surgical tool to the fiducial markers to determine their position. The position and orientation of the reference object 226 is monitored by the localizer. As is well known by those skilled in the art, the patient and operating room reference frames may be automatically re-correlated by the image guided surgery system computer to account for changes in the position of the reference object. Thus, the system automatically accounts for changes in the position of the patient.

The invention has been described with reference to the preferred embodiment. Obviously, modifications and alterations will occur to others upon reading an understanding the preceding description. It is intended that the invention be construed as including all such modifications an alterations insofar as they come within the scope of the appended claims or the equivalents thereof.

What is claimed is:

1. A position signaling apparatus for use with a surgical head clamp, which head clamp includes a frame and a first head engaging pin secured to one side of the frame, the apparatus comprising:

pin holding means mountable to an opposite side of the frame, the pin holding means pin holding means mountable to an opposite side of the frame, the pin holding means adapted to support second and third head engaging pins mountable thereon;

a position signaling device supported by the pin holding means, the signaling device including means for operative communication with an image guided surgery system.

2. The position signaling apparatus of claim 1 including means for selectively adjusting the position of the position signaling device in relation to the pin holding means.

3. The position signaling apparatus of claim 1 comprising means for attaching the signaling device to the pin holding means.

4. The position signaling apparatus of claim 3 wherein the means for attaching comprises a clamp attached to the pin holding means.

5. The position signaling apparatus of claim 1 further comprising an adjustable support structure which attaches the position signaling device to the pin holding means, the adjustable support structure comprising:

first and second members;

a joint which connects the first and second members, the joint selectively allowing relative pivotal motion therebetween.

6. The position signaling apparatus of claim 5 wherein the first member defines a first longitudinal axis and the joint selectively allows relative motion of the joint and the first member along the first longitudinal axis.

7. The position signaling apparatus of claim 6 wherein the second member defines a second longitudinal axis and the joint selectively allows relative motion of the joint and the second member along the second longitudinal axis.

8. The position signaling apparatus of claim 7 wherein the joint selectively allows relative rotational motion of the first member and the joint about the first longitudinal axis.

9. The position signaling apparatus of claim 8 comprising a third member and a second joint interconnecting the second and third members, the joint selectively allowing relative pivotal motion therebetween.

10. The position signaling apparatus of claim 5 wherein the members comprise rigid, cylindrical rods.

11. The position signaling apparatus of claim 5 wherein the joint comprises a clamp.

12. The position signaling apparatus of claim 1 wherein the pin holding means comprises a mounting boss and the position signaling device is supported by the mounting boss.

13. The position signaling apparatus of claim 1 wherein the position signaling device comprises a plurality of infrared emitters.

14. A method of determining the position of an object disposed in a surgical head clamp, the head clamp including a frame, a first head engaging pin secured to one side of the frame, and a pin holding means mounted to an opposite side of the frame, the pin holding means supporting second and third head engaging pins mounted to the pin holding means, the method comprising the steps of:

mounting a position signaling device to the pin holding means, the position signaling device adapted for operative communication with an image guided surgery system; and using the image guided surgery system to determine the position of the position signaling device.

15. The method of claim 14 wherein the position signaling device is connected to a support and further comprising the step of clamping the support to the pin holding means.

16. The method of claim 15 wherein the pin holding means comprises a mounting boss and the support structure is clamped to the mounting boss.

17. The method of claim 14 wherein the position signaling device is connected to a support structure having an end, the pin holding means comprises a through hole, and the step of mounting comprises inserting the end of the support member into the through hole.

18. The method of claim 14 wherein the pin holding means comprises a mounting boss and the step of mounting comprises:

connecting a first rod to the mounting boss;

connecting a second rod to the first rod, the first and second rods being selectively movable with respect to each other;

connecting the second rod to a third rod, the second and third rods being selectively movable with respect to each other;

connecting the third rod to the position signaling device;

adjusting the position of the signaling device in relation to the pin holding means.

19. A position signaling apparatus comprising: a clamp including a frame, a first object engaging pin disposed on one side of the frame, second and third object engaging pins, and pin holding means movably mounted to an opposite side of the frame, the pin holding means adapted to support the second and third object engaging pins mounted thereon, the apparatus further comprising:

a position signaling device disposed in fixed relation to the pin holding means for movement therewith;

means for determining the position of the position signaling device, the determining means in operative relationship with the position signaling device.

20. The position signaling apparatus of claim 19 including means for selectively adjusting the position of the position signaling device in relation to the pin holding means.

21. The position signaling apparatus of claim 19 wherein the means for determining comprises an infrared localizer.

22. The position signaling apparatus of claim 19 comprising a mounting structure which attaches the position signaling device to the pin holding means, the mounting structure comprising a plurality of connected cylindrical rods having longitudinal axes, the connections selectively allowing the rods to be rotated about their longitudinal axes, the connections further selectively allowing relative pivotal motion of adjacent connected rods.

23. The position signaling apparatus of claim 22 wherein the connections selectively allow the rods to be moved along their longitudinal axes.

24. An position signaling position signaling apparatus for use with an image guided surgery system, the apparatus comprising:

a position signaling device adapted for operative communication with the image guided surgery system; and an adjustable support structure comprising a first member connected to the position signaling device;

a second member;

a joint disposed between and connecting the first member and the second member, the joint selectively allowing relative pivotal motion of the first and second members.

25. The position signaling apparatus of claim 24 wherein the second member may be readily disconnected from and connected to the first member.

26. The position signaling apparatus of claim 24 wherein the first member has a longitudinal axis and the joint is adapted to selectively allow relative rotational motion of the joint and the first member about the longitudinal axis.

27. The position signaling apparatus of claim 26 wherein the second member has a longitudinal axis and the joint is adapted to selectively allow relative rotational motion of the joint and the second member about the longitudinal axis of the second member.

28. The position signaling apparatus of claim 27 wherein the joint is adapted to selectively allow relative motion of the second member and the joint along the longitudinal axis of the second member.

29. The position signaling apparatus of claim 26 wherein joint is adapted to selectively allow relative motion of the first member and the joint along the longitudinal axis.

30. The position signaling apparatus of claim 24 further comprising a third member;

a joint disposed between and connecting the second member and the third member, the joint selectively allowing relative pivotal motion of the second and third members.

31. The position signaling apparatus of claim 24 wherein the position signaling device comprises a threaded aperture and the first member comprises a cylindrical rod adapted to engage the threaded aperture.

32. The position signaling apparatus of claim 24 wherein the joint comprises a clamp having a thumb screw.

* * * * *